United States Patent [19]

Watanabe et al.

[11] Patent Number: 4,499,181
[45] Date of Patent: Feb. 12, 1985

[54] PHOTOGRAPHIC RECORDING MATERIAL WITH INDOLE REDOX RELEASER

[75] Inventors: Kazumasa Watanabe, Tokyo; Hidetaka Deguchi, Tama; Shunji Suginaka, Tokyo, all of Japan

[73] Assignee: Konishiroku Photo Ind., Co., Ltd., Tokyo, Japan

[21] Appl. No.: 500,406

[22] Filed: Jun. 2, 1983

Related U.S. Application Data

[63] Continuation of Ser. No. 322,709, Nov. 18, 1981, abandoned.

[30] Foreign Application Priority Data

Nov. 18, 1980 [JP] Japan ................ 55-162940

[51] Int. Cl.$^3$ .............. G03C 5/54; G03C 1/40; G03C 1/10; G03C 1/42
[52] U.S. Cl. .................... 430/558; 430/218; 430/219; 430/223; 430/217; 430/234; 430/559; 430/564; 430/566; 430/598; 430/607; 430/621; 430/957; 430/958; 430/959
[58] Field of Search ........... 430/223, 218, 219, 251, 430/217, 234, 558, 559, 566, 564, 598, 607, 621, 958, 957, 959

[56] References Cited

U.S. PATENT DOCUMENTS

| | | | |
|---|---|---|---|
| 4,179,291 | 12/1979 | Vetter et al. | 430/223 |
| 4,198,235 | 4/1980 | Vetter et al. | 430/223 |
| 4,273,855 | 6/1981 | Jaeken et al. | 430/223 |
| 4,277,553 | 7/1981 | Onodera et al. | 430/223 |
| 4,360,581 | 11/1982 | Odenwalder et al. | 430/223 |

Primary Examiner—Richard L. Schilling
Attorney, Agent, or Firm—Finnegan, Henderson, Farabow, Garrett & Dunner

[57] ABSTRACT

A photographic recording material. On a support are provided a silver emulsion halide layer and a photographic layer. The photographic layer contains an indole compound represented by the general formula (I):

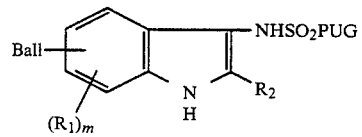

wherein PUG represents a photographically useful group, Ball represents an organic group which has enough molecular weight and/or disposition to render the compound non-diffusible during processing of the photographic recording material with an alkaline medium and wherein the Ball contains a nitrogen atom which is directly attached to the 5th or 6th position of the indole ring. $R_1$ represents a halogen atom or a monovalent organic group. $R_2$ represents a hydrogen atom or a low molecular group attached, through a carbon atom, to the 2nd position of the indole ring. "m" represents an integer of zero to 3.

8 Claims, No Drawings

PHOTOGRAPHIC RECORDING MATERIAL WITH INDOLE REDOX RELEASER

This is a continuation of application Ser. No. 322,709, filed Nov. 18, 1981, now abandoned.

The present invention relates to a photographic recording material, and more particularly to a silver halide photographic recording material containing a compound which releases efficiently a photographically useful group.

Nondiffusible compounds which release diffusible dyes or other photographically useful groups as result of the oxidation and alkali hydrolysis, and dye diffusion transfer processes which utilize these compounds are disclosed in Japanese Patent Publications Open To Public Inspection (hereinafter referred to as Japanese Patent O.P.I. Publication) No. 104343/1976, No. 33826/1973, No. 130122/1979, No. 3819/1978 and 54021/1979.

One of the useful group of such compounds is an indole compound having at least one ballast groups, and having, in the 3rd position thereof, a photographically useful group (hereinafter referred to as "PUG" group) through a sulfonamide group.

The ballast group attached to these compounds is an organic stabilizing group having a molecular weight and disposition such that the compound is nondiffusible in an alkali medium during development. Usually, the ballast group is an organic group having 8 to 40 carbon atoms.

These compounds are considered to be oxidized at the time of development and subjected to hydrolysis by alkali to release imagewise a photographically useful substance represented by a formula $H_2NSO_2PUG$.

Compounds are desired that can release the photographically useful group more rapidly, have higher silver utilization efficiency, and provide a clearer image.

It is an object of the present invention to provide a photographic recording material capable of meeting such a demand.

The object of the present invention can be accomplished by a photographic recording material which comprises an indole compound having the following general formula (I) (hereinafter referred to as the compound of the invention):

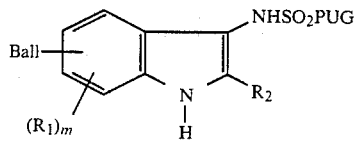
(I)

wherein PUG represents a photographically useful group, Ball represents a ballast group attached through a nitrogen atom to the 5th or 6th position of the indole ring, $R_2$ is a hydrogen atom or a low molecular group attached through carbon atom, $R_1$ is a halogen atom or a monovalent organic group, and m is an interger of from zero to 3. The Ball represents an organic group which has enough molecular weight and or disposition to render the compound nondiffusible during development in an alkali medium (hereinafter referred to as "stabilization group".

The following are detailed descriptions of the indole compound of Formula (I).

In Formula (I), the stabilization group is preferably selected from those groups having an aliphatic, aromatic, alicyclic or heterocyclic group having from 8 to 20 carbon atoms. These groups are attached through a nitrogen atom to the 5th or 6th position of the indole ring, preferably, through such nitrogen-atom-containing groups as $-NHCO-$, $-NHSO_2-$, $-NR_5-$ wherein $R_5$ represents hydrogen or alkyl. Ball may be attached to the 5th to 6th position of the indole ring, and the 5th position is more preferable.

The monovalent organic group represented by $R_1$ which is preferable in the invention includes alkyl and alkoxy gorups, etc., among which an alkyl or alkoxy group having 1 to 3 carbon atoms is preferred.

Representative $R_2$ low molecular groups attached through a carbon atom include groups having from 1 to 9 carbon atoms, such as an alkyl or a phenyl each having from 1 to 9 carbon atoms or

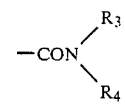

wherein $R_3$ and $R_4$ independently represent a hydrogen atom or an alkyl group having from 1 to 4 carbon atoms and provided that $R_3$ and $R_4$ may form a ring.

$R_2$ is, more preferably, selected from a phenyl group which is unsubstituted or substituted by a halogen atom, or an acetylamide, methyl sulfonamide, nitro, carboxy, sulfo, methanesulfone, alkyl or alkoxy group.

The photographically useful group presented by PUG is capable of causing a photographic effect and includes, for example, silver-complex forming agents, silver halide-solving agent, hardeners, fogging agents, anti-foggants, developers, development restrainers, development accelerators, bleach restrainers, bleach accelerators, dyes and dye precursors.

Among these photographically useful groups, dyes or dye precursors having an alkali-soluble group are preferred, which compounds of the present invention are called Dye Releasing Redox compounds (hereinafter referred to as DRR compounds).

The foregoing dyes include, for example, azo dyes, azomethin dyes, indoaniline dyes, indophenol dyes, anthraquinone dyes, triarrylmethane dyes, alizarin dyes, merocyanine dyes, nitro dyes, quinoline dyes, cyanine dyes, indigo dyes, and metal complex dyes while the dye precursors include known leuco dyes, shift dyes and the like. These are disclosed in Japanese Patent O.P.I. Publication No. 33141/1980, No. 33142/1980, No. 33533/1978, No. 53329/1980 and the like.

The most preferred compound among formula (I) is selected from those compounds having the following formula (II);

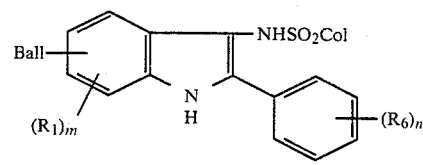
(II)

wherein Ball represents an alkyl acylamide, aryl acylamide, succinimide or phthalimide group, $R_1$ is a halogen atom, or an alkyl or alkoxy group having from 1 to 3 carbon atoms; $R_6$ represents halogen atom, or an alkyl or alkoxy having from 1 to 2 carbon atoms, acetylamide, methyl sulfonamide, nitro, carboxyl, sulfo or methylsulfonyl gorup; n and m independently an integer of from zero to two, and Col represents a dye or dye precursor.

The alkyl group in the alkyl acylamide in Ball includes those alkyl groups of straight or branched chain, having from 12 to 20 carbon atoms, while the aryl of the aryl acylamide may be substituted by those alkyl, alkoxy, alkyl acylamide and alkyl sulfonamide groups each having from 5 to 20 carbon atoms.

The imide of the succinimide and phthalimide may be substituted by an alkyl, alkoxy, alkyl acylamide or alkyl sulfonamide group and having from 5 to 20 carbon atoms.

In Formula (II), the dye and dye precursor represented by Col is the same as those described in Formula (I).

The indole compound of the present invention is characterized by the position thereof to which the ballast group is attached, i.e. the ballast group is attached to the 5th or 6th position of the indol ring, resulting in the attainment of efficient release of the photographically useful group.

Although the reason for this phenomenon is uncertain, it is assumed that in the compound of the present invention, as shown below, the indole —NHSO₂PUG (III) is first oxidized to quinonediimine structure (IV) and is then subjected to hydrolysis by alkali to release a —NH₂SO₂PUG group.

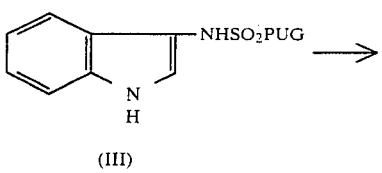

(III)

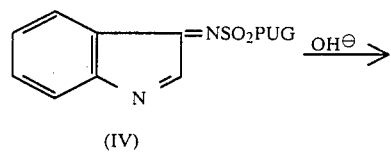

(IV)

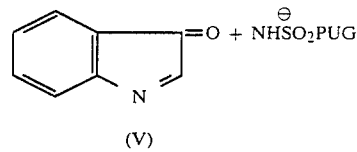

(V)

In the compound of the present invention, the position of the ballast group is geometrically far away from the —NHSO₂PUG, facilitating the attack by OH against the carbon atom of the —C=N— bond of the oxidized compound (IV). It is considered that this reaction mechanism is of importance in obtaining the excellent effect of the present invention.

When the photographically useful group is a dye and is used in a diffusion transfer photographic process, the compound of the present invention provides such excellent effects as rapid image formation with less fog and color images with sufficient density.

The following are preferred examples of the compound of the present invention:

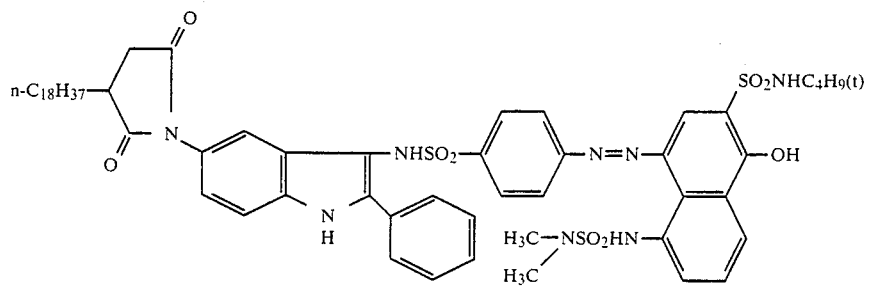

(1)

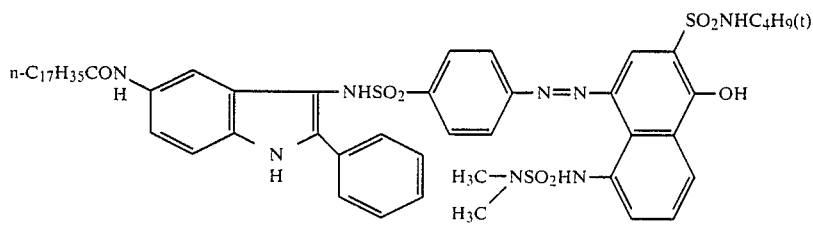

(2)

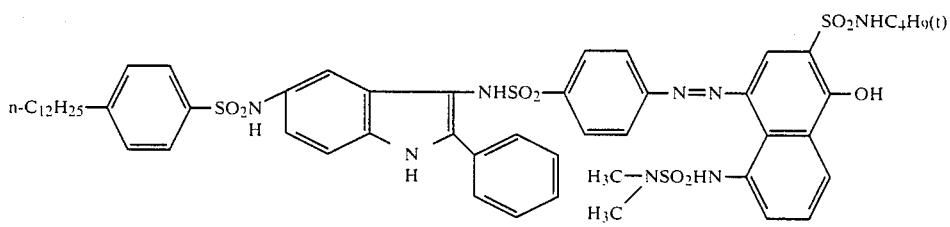

(3)

-continued
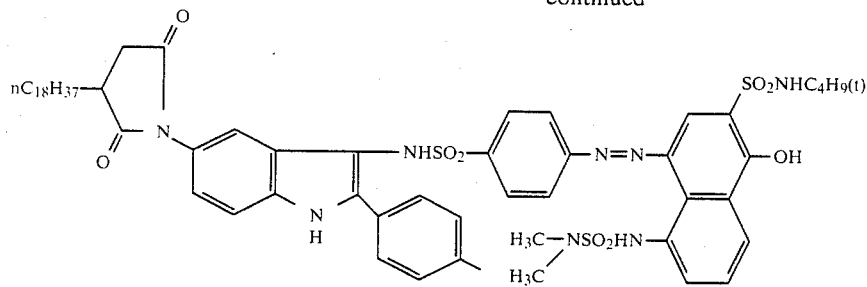
(4)
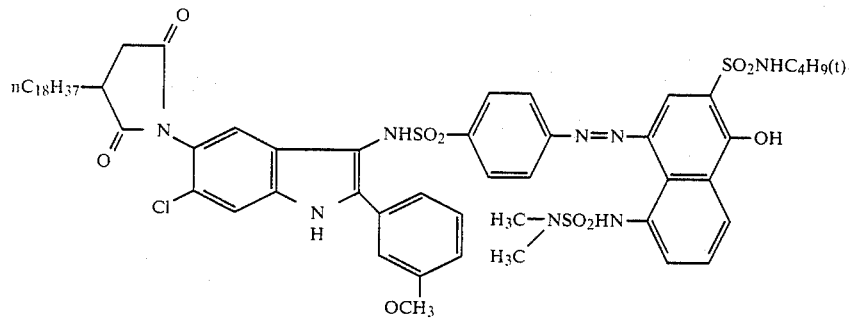
(5)
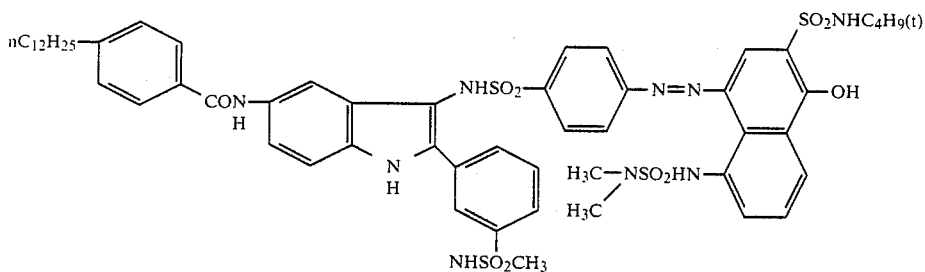
(6)
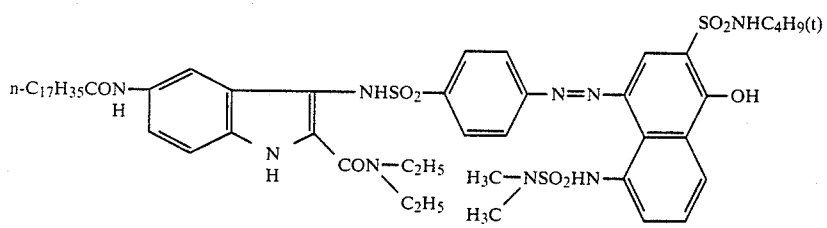
(7)
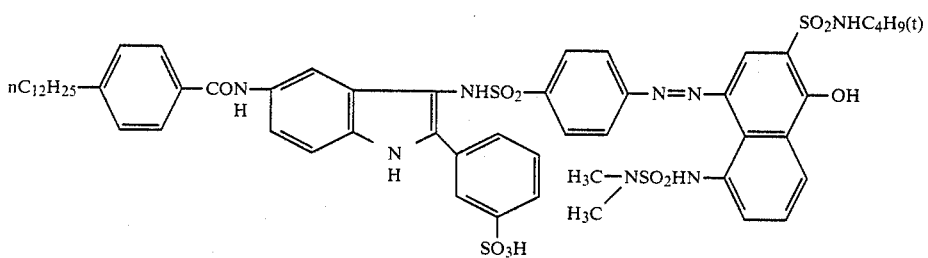
(8)
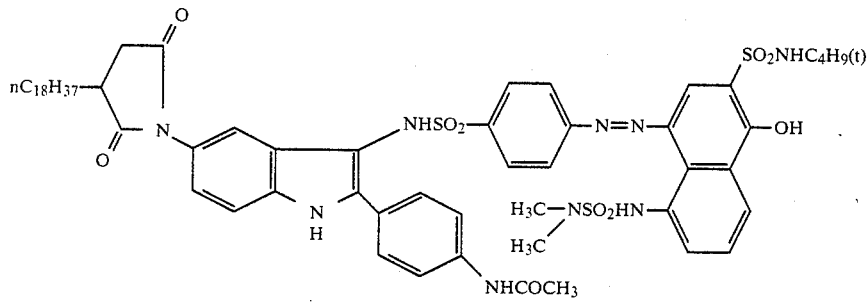
(9)

-continued
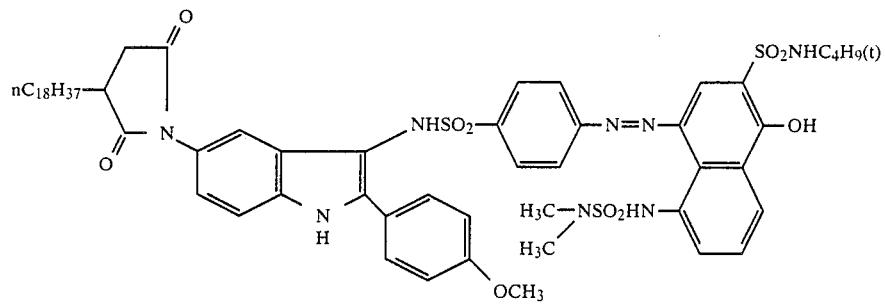 (10)
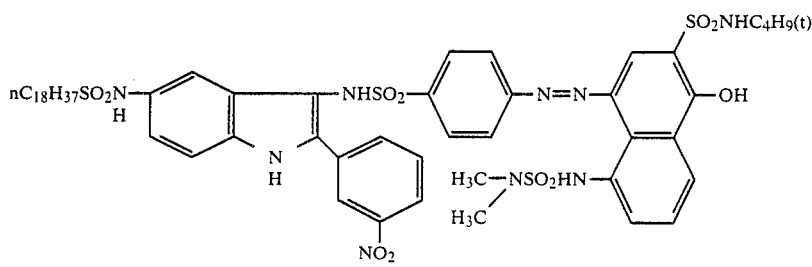 (11)
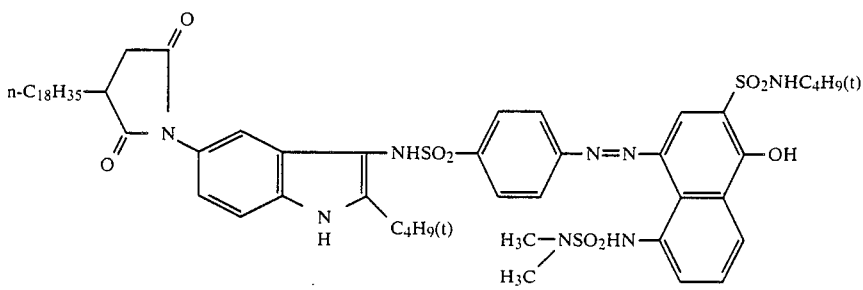 (12)
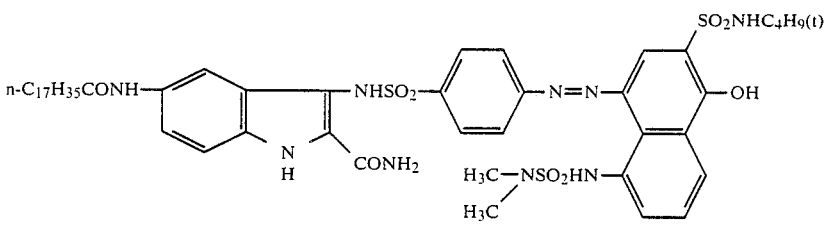 (13)
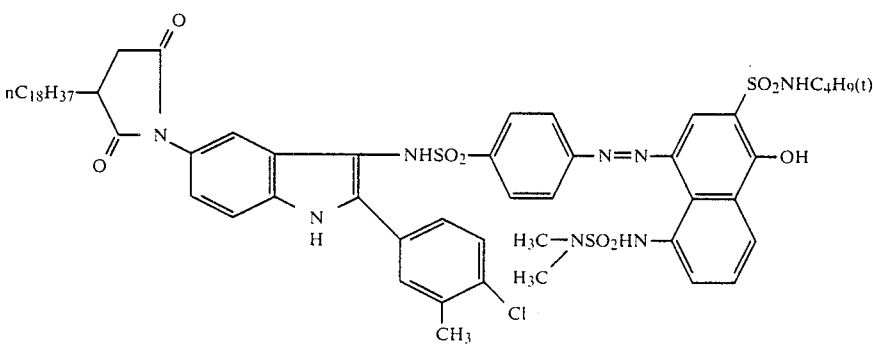 (14)

-continued
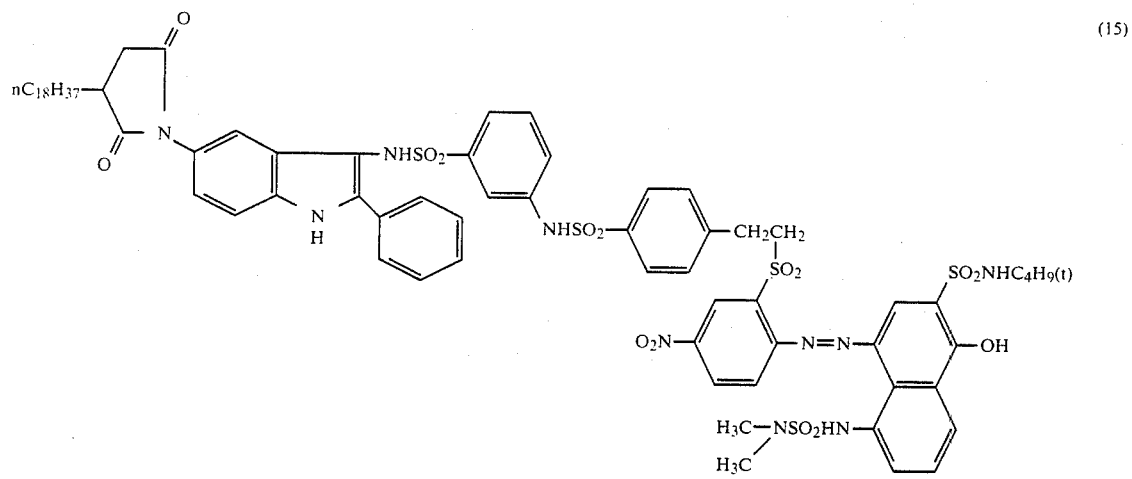
(15)
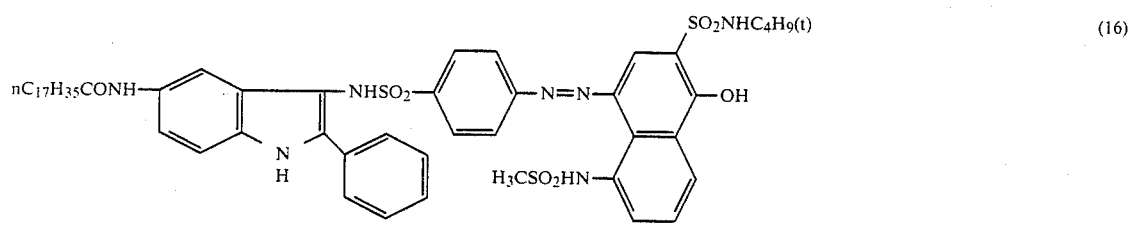
(16)
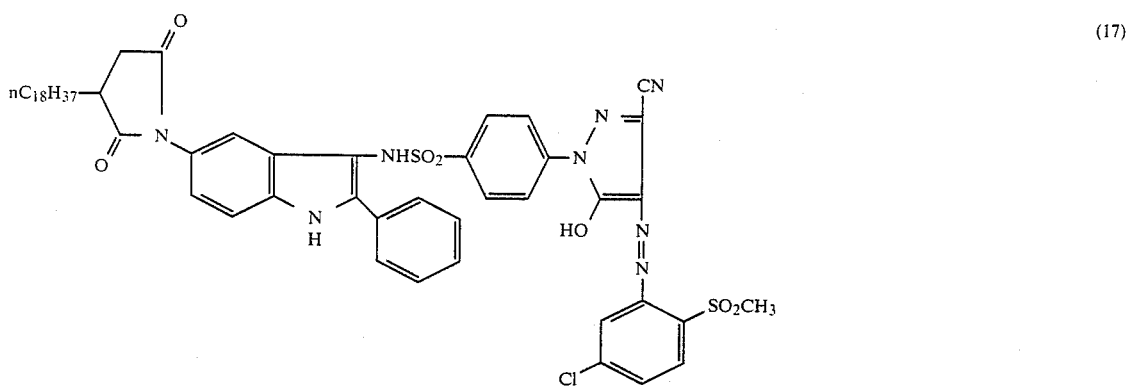
(17)
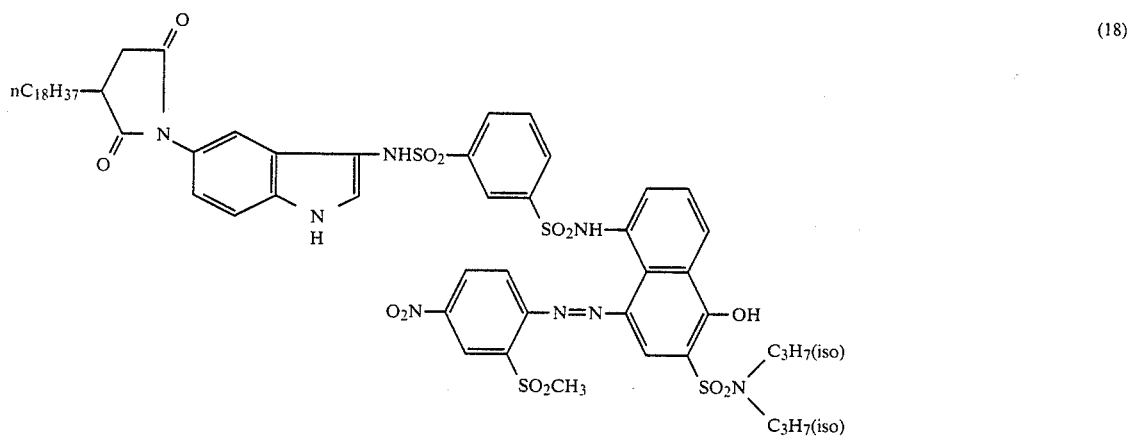
(18)

-continued

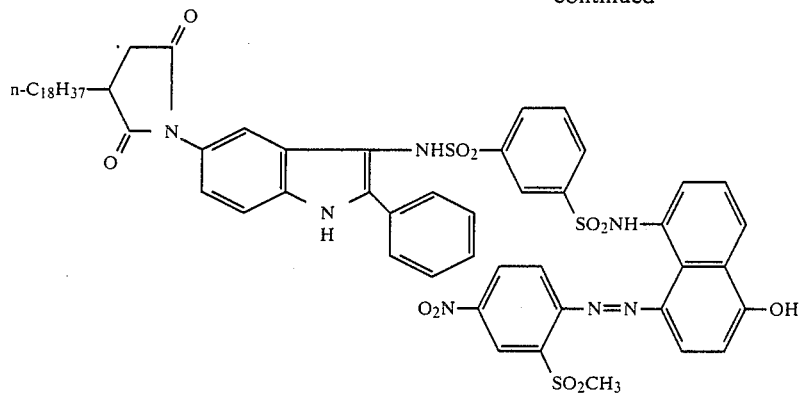
(19)

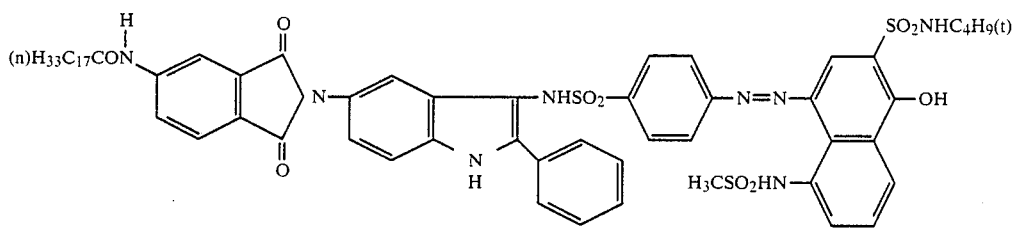
(20)

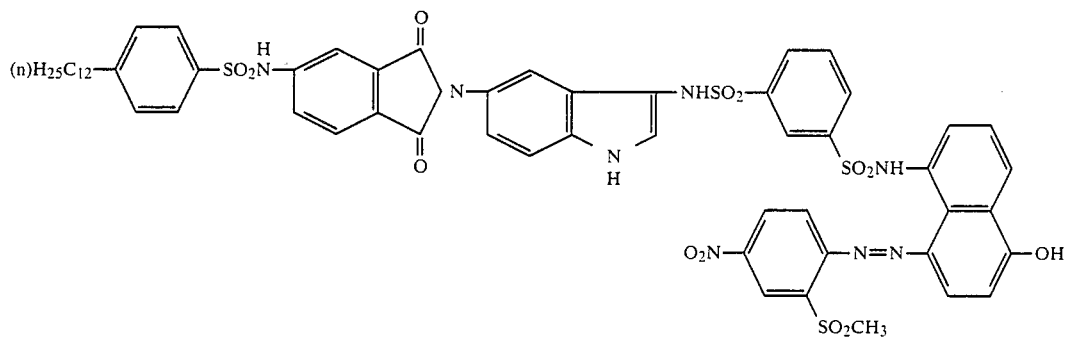
(21)

The indole ring, which is an important intermediate in the synthesis of the compounds of the invention, may be synthesized by various methods.

For example, some indole rings may be formed from hydrazones in the presence of an acid catalyst in the Fischer indole synthesis. These hydrazone compounds may be obtained by the condensation of acetophenone and hydrazine (J. Chem. Soc., 1959, 3388), and may also be obtained through the diazo coupling by the Japp-Klingemann reaction (Org. Reaction., Vol 10, 143: J. Am. Chem. Soc., 75, 2502). Other indole rings are obtained by the method discovered by Roger Adams, i.e., the addition product obtained from the reaction of quinone diimide with an activated methylene compound is formed into a closed ring by the use of an acid catalyst (J. Am. Chem. Soc. 77, 5375, 5383).

The following are synthesis examples:

SYNTHESIS EXAMPLES

1. Synthesis of Exemplified Compound (1)

1-1 Synthesis of p-phenylene bis-(dimethyl sulfamamide)

Under nitrogen gas flow 108 g of p-phenylenediamine was dissolved in 1.2 liters of pyridine and a solution was cooled to below 20° C. with ice, and 390 g of dimethyl aminosulfonyl chloride was added dropwise to the mixture. After being left overnight at below 20° C. the resulting mixture was heated up to 30° C. and at the same temperature the mixture was stirred for a period of two hours, thereby completing the reaction. A 25% aqueous sodium hydroxide solution was subsequently added to the mixture, which was further stirred for two hours.

The thus obtained dark solution was poured under agitation into a mixture of iced water with hydrochloric acid (3 liters of concertrated hydrochloric acid and 18 liters of iced water) and was then filtered. The resulting residuum was washed with dilute hydrochloric acid, and finally with water, thus obtaining 320 g of a dark crude product. This product and 100 g of charcoal were subsequently suspended in 4 liters of heated acetone, and the suspension was filtered to obtain a residuum, which was further washed with 2 liters of heated acetone. The filtrate thus obtained was concentrated to a one-liter volume, to which was then added 1 liter of water to thereby deposit crystals. After being allowed to stand overnight, filtering was used to thereby obtain 425 g of light pink-colored prism (m.p. 240° to 242° C.). The yield was 76%.

1-2 Synthesis of p-quinone bis-(dimethyl sulfamimide)

128 g of the p-phenylene bis-(dimethy sulfamamide) obtained in 1-1 and 190 g of lead tetraacetate were suspended into 600 ml of glacial acetic acid, and the suspension was stirred for one hour under heating at the temperature of 50° to 55° C. The thus obtained yellow suspension was cooled to 17° C., filtered, washed with 100 ml of glacial acetic acid, and then with 1 liter of water, thereby obtaining 123 g of yellow needle crystals (m.p. 181° C.) with a yield of 96%.

1-3 Synthesis of benzoyl ethyl acetate addition product of p-quinone bis-(dimethyl sulfamimide)

48.0 g of the quinone compound obtained in 1-2 was suspended into 240 ml of dioxane, and to the suspension were added dropwise 30 g of benzoyl ethyl acetate. The mixture was cooled to 15° C. and to it was added 0.5 g of sodium methylate.

Upon the addition the reaction temperature was increased to 30° C., causing the reaction mixture to become a dark solution, which was then stirred for 10 minutes at 20° to 30° C., to which was subsequently added 3 ml of glacial acetic acid, and was further stripped for 30 minutes, and thereafter was poured into 500 ml of n-hexane. The white precipitate was filtered and washed with 400 ml of n-hexane to thereby obtain 77.0 g of a white powder with a yield of 100% (m.p. 113° to 115° C.).

1-4 An 5-amino-2-phenyl indole 51.2 g of the addition product obtained in 1-3 was suspended into a mixture of 200 ml of glacial acetic acid and 200 ml of concentrated hydrochloric acid, and the suspension was refluxed for a period of 7 hours. Subsequently, 100 ml of concentrated hydrochloric acid were further added and another 7-hour reflux was carried out. After being allowed to stand overnight, the produced white needle cyrstals were filtered and then washed with 50 ml of a concentrated hydrochloric acidglacial acetic acid mixture solvent (3:2) to thereby obtain 19.0 g of white needle crystals with a yield of 77.8%.

1-5 Synthesis of 5-octadecyl succinimide-2-phenyl indole 16.1 g of the 5-amino-2-phenyl indole hydrochloride obtained in 1-4 and 24.85 g of octadecyl succinic acid anhydride were suspended into 120 ml of glacial acetic acid, and to the suspension were added dropwise 40 ml of triethylamine.

The mixture was then gradually heated to be subjected to reflux, spending one hour, and to an additional 30-minute reflux. Subsequently 30 ml of acetic anhydride was added to the mixture, which was further subjected to 2-hour reflux. After cooling, the produced precipitate was filtered, washed with 100 ml of glacial acetic acid and then with 100 ml of water, thus producing 31.0 g of white needle crystals with a yield of 85% (m.p. 156° to 160° C.).

1-6 Synthesis of an intermediate 5-octadecyl succinimide-2-phenyl-3-nitrosoindole 32.5 g of the 5-octadecyl succinimide-2-phenyl indole obtained in 1-5 were suspended into 1.1 liters of glacial acetic acid, and to the suspension with vigorously stirring at 25° to 30° C. were added portionwise 4.9 g of sodium nitrite. After the addition thereof, at the same temperature the mixture was further stirred for two hours and then cooled to 18° C. The resulting suspension, orange in color, was filtered, washed with 200 ml of glacial acetic acid, then with 500 ml of water, and finally with 100 ml of methanol, whereby 32.5 g of yellow needle crystals (m.p. 205° to 207° C.) were obtained with a yield of 95%. 1-7 Synthesis of an intermediate 3-amino-5-octadecyl succinimide-2-phenyl indole 32.5 g of the 5-octadecyl succinimide-2-phenyl-3-nitrosoindole obtained in 1-6 was suspended into 700 ml of ethanol, and the suspension was vigorously sitrred, to which were then added a solution of 50 g of sodium hydrosulphite dissolved into 200 ml of water, and the mixture was refluxed for two hours and cooled. The white suspension produced was filtered, sufficiently washed with water and finally with 50 ml of methanol, and then rapidly dried at room temperature, thereby obtaining 29.5 g an objective white product (m.p. 150° to 152° C.) with a yield of 93%.

1-8 Synthesis of compound (1)

27 g of the 3-amino-2-octadecyl succinimide-2-phenyl indole obtained in 1-7 was dissolved into 300 ml of chloroform, and to the solution were added 20 ml of pyridine and further added with little stirring at room temperature 31 g of 2-tert-butyl sulfamoyl-5-(N,N-dimethylamino-sulfonamide)-4-(4-chlorosulfonyl phenylazo)-1-naphthol (Japanese Patent O.P.I. Publication No. 33142/1980). After 2-hours stirring at 30° to 40° C. and 2-hour reflux with heating, the mixture was allowed to stand overnight. The mixture, after the addition of 200 ml of methanol and 30 ml of water thereto, was refluxed for one hour to decompose completely the unreacted sulfonyl chloride. After that, with adding methanol, the mixture was boiled to distill off the chloroform. When the distilling temperature became 62° C., the mixture was cooled to room temperature, to which was then added 25 ml of hydrochloric acid to thereby deposit a precipitate, which was filtered, washed with methanol and with water, and then dried. The resulting product was subsequently refined by use of a silica gel column. The yield was 35. g, 63% (m.p. 158° to 163° C.).

2. Synthesis of Exemplified Compound (16)

2-1 Synthesis of 5-stearylamide-2-phenyl indole 4.17 g of the 5-amino-2-phenyl indole (it was formed from its hydrochloride and alkali) obtained in 1-4 were dissolved into 30 ml of THF, and to the solution was added 3 ml of triethylamine. The mixture was added cooled to 0° C., and to this was dropwise a solution of 6.5 g of stearyl chloride dissolved into 8 ml of benzene. The resulting mixture was then brought back to room temperature and stirred for two hours. The crystals thus produced were filtered, washed with methanol, with dilute hydrochloric acid, and finally with water to thereby obtain 6.8 g of white needle crystals (m.p. 187° to 188° C.) with a yield of 72%.

2-2 Synthesis of 5-stearylamide-2-phenyl-3-nitrosoindole 6.15 g of the 5-stearylamide-2-phenyl indole obtained in 2-1 was suspended into 30 ml of glacial acetic acid, and to the suspension 1.1 g of sodium nitrite was gradually added at the temperature of 25° to 30° C. After two-hours of stirring, the suspension was cooled to 18° C. The resulting yellow suspension was filtered, washed with 10 ml of glacial acetic acid, with water and finally with 10 ml of methanol to thereby obtain 6.05 g of yellow crystals (m.p. 255° to 258° C. (d)) with the yield of 93%.

2-3 Synthesis of an intermediate 3-amino-5-stearylamide-2-phenyl indole 6.02 g of the foregoing nitroso compound obtained in 2-2 was suspended into 250 ml of ethanol and the suspension was vigorously stirred, to which was added a solution of 15 g of sodium hydrosulfite dissolved in 60 ml of water, and the mixture was refluxed for two hours, and cooled. The thus produced white suspension was then filtered, washed sufficiently with water and finally with 10 ml of methanol, and then dried quickly at room temperature, whereby 5.4 g of an objective, white product with a yield of 92% (m.p. 193° to 198° C.) was obtained.

2-4 Synthesis of compound (16)

16.5 g of the 3-amino-5-stearylamide-2-phenyl indole obtained in 2-3 was dissolved into 250 ml of chloroform, and to the solution were added 10 ml of pyridine and further added little by little at room temperature 19.5 g of 2-tert-butyl sulfamoyl-5-methyl sulfonamido-4-(4-chlorosulfonyl phenylazo)-1-naphthol. After two-hours of stirring at 30° to 40° C. and a two-hour reflux with heating, the mixture was allowed to stand overnight. Subsequently, the mixture, to which was added 200 ml of methanol and 20 ml of water, was refluxed for a period of one hour to completely decompose the unreacted sulfonyl chloride. After that the mixture was boiled with adding methanol to distill off the chloroform. After the distillation (distilling temperature: 61° C.), the mixture was cooled and to this were added 15 ml of hydrochloric acid to deposit a precipitate which was then filtered, washed with methanol and with water, then dried and finally refined by the use of a silica gel column to thereby obtain 21 g of an objective product with the yield of 62% (m.p. 179° to 181° C.).

Where the photographic recording material of the present invention is used as a color diffusion transfer photographic material, various conventionally known color diffusion transfer photographic materials may be used. Preferred diffusion transfer materials include the following two types of photographic materials. The first type usually comprises a first support coated thereon with a light-sensitive emulsion layer containing silver halide associated with a DRR compound and a second support coated thereon with an image receiving layer. The second type comprises a support and a processing sheet, the support being coated on one side thereof with a light-sensitive emulsion layer containing siver halide associated with a DRR compound, and an image receiving layer on the same side thereof. In the first type color diffusion transfer photographic material, at the time of processing, both supports are disposed so that both the light-sensitive silver halide emulsion layer and the image receiving layer are positioned therebetween, while in the second type color diffusion transfer photographic material, the support and the processing sheet are disposed so that both the light-sensitive silver halide emulsion layer and the image receiving layer are positioned therebetween.

As the support of the photographic recording material of the present invention there may be used any support applied to conventionally known photographic materials, and the support may be either transparent or opaque.

In the present invention, a neutralizing layer and timing layer may be coated on the support on which the foregoing light-sensitive silver halide emulsion layer and/or image receiving layer is to be coated, or on the processing sheet.

The neutralizing layer is intended to serve effectively for increasing the stability of the color image by lowering the pH after the dye image is substantially formed on the image receiving layer as a result of image formation process by alkaline processing composition; for substantially restricting the limitless diffusion tendency of the diffusible dye and the like; and for the prevention of possible discoloration or stains caused on the image by the high pH. On the other hand, the timing layer is intended to serve for delaying the lowering of the pH until after the desired development and image transfer. That is to say, the timing layer serves for the prevention of the undesirable deterioration of the transfer dye image density due to the rapid reduction of the pH brought about by the neutralizing layer prior to the development of the silver halide and the formation of the diffusion transfer image.

In the case where the color diffusion transfer photographic recording material is used as a color photographic printing paper, a suitable background is needed for the developed image. As the background for the image a highly white light-reflective layer is normally provided on the back of the image receiving layer opposite to the observation side. When, after exposure, the development of the photographic recording material is carried out in the light, the material is desired to be provided with an opaque layer for protecting the silver halide emulsion layer from the light.

As the light-sensitive silver halide emulsion used in the present invention, if desired, conventionally known various ones may be used which may be of either negative or positive type. In the case of using the negative type silver halide emulsion, the development takes place in the exposed portion to release dyes, so that a negative image is normally formed on the image receiving layer. Where the negative type silver halide emulsion is used, a reversal positive image may be obtained by the use of known reversal process. One of such processes includes the silver salt diffusion transfer process, which uses such a photographic recording material as having both a negative type silver halide emulsion layer and associated therewith a layer containing development speck for physical development and a DRR compound. When the material is processed with the development speck containing a silver halide solvent, the silver halide in the unexposed portion becomes dissolved to be transferred to the different layer where physical development takes place. As a result of this, development takes place as an inverse function of the exposure, and so that a positive image is obtained (cf. Japanese Patent O.P.I. publication No. 325/1972).

In addition, as is described in Japanese Patent Examined Publication No. 21788/1968 and U.S. Pat. No. 3,227,554 and the like, such photographic recording material as comprises a fogged negative type silver halide emulsion layer containing a color image-providing material, and an adjacent layer containing a compound which releases a development inhibitor as a result of a reaction with an oxidized product of the silver halide developing agent can be mentioned.

Also in this method a positive image may be obtained as an inverse function of the exposure, however, in this invention it is preferable to use a positive type light-sensitive silver halide emulsion, particularly, an internal-image type direct positive silver halide emulsion.

In the case of obtaining a multi-color dye image, using the color diffusion transfer photographic material according to the present invention, it is desirable to use two or more units of different combination of light-sensitive silver halide emulsion and DRR compound, and when the spectral sensitivity of each unit differs, it is preferable to employ an interlayer between each unit. The interlayer serves for preventing possible undesirable interaction between the units as well as for controlling the diffusion of the diffusible dyes or the precursors thereof and alkaline processing composition. In the color diffusion transfer photographic recording material according to the present invention, a protective layer may optionally be employed in the position where a processing composition is to be distributed.

The layer containing a DRR compound may be disposed adjacent to the light-sensitive silver halide emulsion layer.

The color diffusion transfer photographic recording material according to the present invention may be provided with an image receiving layer containing a mordant in order to fix the dye which diffuses through the alkaline medium. Various mordants may be selected according to the type of the dye used, and when mordanting an acid dye, it is desired to use basic polymer mordants such as those described in, for example, Japanese Patent O.P.I. Publication No. 124726/1979 and No. 74430/1979.

Where the acid dye is leuco dye, a suitable oxidizing agent may be incorporated into the image receiving layer or the layer adjacent thereto.

To process the color diffusion transfer photographic recording material according to the present invention, an alkaline processing composition is usually used. This composition preferably has a pH of 10 or more at room temperature and preferably contains a viscosity controlling agent and has a viscosity value of from 100 to 300,000 centipoise. Thereby, the distribution of the processing composition at the time of processing can be made uniform. This uniform distribution forms a nonfluid membrane during the processing, and plays an effective role for the prevention of possible undesirable changes in the image during the formation thereof.

As a means of applying the processing composition to photographic materials, conventionally known ones may be used, but preferably the composition is contained in a container which is rupturable at the time of processing.

In order for the DRR compound according to the present invention to release a diffusible dye, since the compound itself is hard to react directly with silver halide, it is usually necessary to use a developing agent for cross-oxidation. As the developing agent, various silver halide developing agents may be selected, and for preventing of of the occurrence of possible color stains, a developing agents usually used in black-and-white photography, particularly phenidones (for example, those disclosed in Japanese Patent O.P.I Publication No. 52055/1980) may suitably be used.

The developing agent can be incorporated into various layers, but is usually incorporated into the processing composition. The processing compoposition, if necessary, may contain various additives usually used, e.g., a reflection agent such as titanium oxide, an opacifying agent such as carbon black or an indicator dye, etc.

Further, in the color diffusion transfer photographic recording material according to the present invention, for the purpose of obtaining a satisfactory color image, a development inhibitor precursor (for example those disclosed in Japanese Patent O.P.I publication No. 46842/1979), which releases a development inhibitor after a definite interval in the alkaline solution may be employed. This development inhibitor precursor may be incorporated into various layers, and is usually incorporated into a layer separated from the silver halide emulsion layer or added to the layer provided on a different support.

The DRR compound used in the present invention, as mentioned hereinbefore, releases a dye in the area in which development takes place, which dye thereafter is to be diffused to the image receiving layer where it is fixed to form a dye image. Beside this, this DRR compound may also be utilised in a method wherein an image is formed by the remaining DRR compound in the undeveloped area. In this method the image is obtained by removing the residual silver and silver halide by the use of a process well known in field, such as by bleaching or bleach-fixing process.

The present invention is further illustrated hereinbelow with reference to examples.

EXAMPLE 1

A multi-layered light-sensitive element was prepared by coating, in order, the following layers on a 110-micron-thick transparent polyethylene terephthalate film support. In this and following examples, unless defined otherwise, figures in the parentheses represent the coated amount of materials used.

(1) An image receiving layer comprising a poly[styrene-co-N,N,-dimethyl-N-benzyl-N-p-(methacryloylaminophenyl)methyl ammonium chloride-divinyl benzene] (molar ratio:48:48:4) (27 mg/100 cm$^2$), brightening agent (0.4 mg/100 cm$^2$) and gelatine (27 mg/100 cm$^2$).

(2) A light reflection layer comprising titanium dioxide (230 mg/100 cm$^2$) and gelatin (22 mg/100 cm$^2$).

(3) An opaque layer comprising carbon black (25 mg/100 cm$^2$) and gelatin (17 mg/100 cm$^2$).

(4) A DRR compound-containing layer comprising a DRR compound (3.5–4.0 mg/100 cm$^2$), 2,5-dioctyl hydroquinone (0–1 mol/mol DRR compound), tricresyl phosphate (2.0–2.5 mg/100 cm$^2$) and gelatin (12.0 mg/100 cm$^2$).

(5) A green-sensitive light-sensitive layer comprising a green-sensitive internal latent image type direct positive silver bromide emulsion (7.5 mg/100 cm$^2$ in silver), potassium 2-sec-octadecyl hydroquinone-5-sulfonate (1.4 g/mol of silver), 1-[4-(2-formyl hydrazino)phenyl]-3-phenyl-thiourea (0.9–2.5 mg/mol of silver) and gelatin (15 mg/100 cm$^2$).

Separately, the following layers were coated, in the following order, on a 100-micron-thick transparent polyethylene terephthalate film support to thereby prepare a processing sheet:

(1) A neutralizing layer comprising poly[acrylic acid-co-butyl acrylate] (ratio by weight: 70:30) (200 mg/100 cm$^2$).

(2) A second timing layer comprising cellulose diacetate (acetylated degree: 55 mol %) (57 mg/100 cm$^2$) and poly[styrene-co-maleic anhydride] (1:1) (4.5 mg/100 cm$^2$) and 5-(2-phenyl sulfonyl-ethylthio)-1-phenyl tetrazole (3.4 mg/100 cm$^2$). (3) A first timing layer comprising poly[vinylidene chloride-co-acrylonitrile-co-acrylic acid] (ratio by weight: 79:15:6) (21 mg/100 cm$^2$).

The thus prepared light-sensitive element was subjected, through an optical silver wedge, to exposure to light at a specific amount and the exposed light sensitive element was superposed with the above-prepared processing sheet.

To the superposed sheets was attached a pod containing alkaline processing composition shown below to prepare a photographic material unit.

In this manner Samples 1 to 8 were prepared. Each light-sensitive element contains different DRR compound as shown in Table 1. In addition, a foregoing agent, 1-[4-(2-formyl hydrazino)phenyl]-3-phenyl thiourea and a scavenger, 2,5-dioctyl hydroquinone were added, varying their quantities as shown in Table 1 with respect to each DRR compound. Each of these samples was put through between forcedly juxtaposed rollers to rupture the pod to spread the contents therein out into between the silver halide emulsion layer (5) and the timing layer (3) of the processing sheet to thereby carry out processing.

Reflection densities of thus transferred dye images were measured at intervals.

| Processing Composition: | |
|---|---|
| Carboxymethyl cellulose sodium salt | 60.0 g |
| Carbon black | 171.0 g |
| Add distilled water to make | 1000 ml |

TABLE 1

| Sample No. | Compound Used | Amount of Scavenger-Mol/Mol DRR | Amount of Fogging Agent/Mol of Silver | $D_{max}$ | Fog. | IP | $T_{0.5}$ | $T_{0.8}$ |
|---|---|---|---|---|---|---|---|---|
| 1 | Control | 0 | 1.2 | 0.32 | 0.07 | 20″ | 1′06″ | 2′23″ |
| | Cpd.(1) | | 1.8 | 0.62 | 0.07 | | | |
| | 35 mg | | 2.4 | 0.77 | 0.07 | | | |
| 2 | Control | 1 | 1.2 | 1.10 | 0.22 | 14″ | 55″ | 2′20″ |
| | Cpd.(2) | | 1.8 | 1.49 | 0.46 | | | |
| | 33 mg | | 2.4 | 1.62 | 0.62 | | | |
| 3 | Control | 1 | 0.15 | 1.50 | 0.54 | 8″ | 1′18″ | 2′35″ |
| | Cpd.(3) | | 0.30 | 1.79 | 0.73 | | | |
| | 34 mg | | 0.60 | 1.90 | 0.81 | | | |
| 4 | Control | 0 | 1.2 | 1.62 | 0.32 | 13.5″ | 1′01″ | 2′19″ |
| | Cpd.(4) | | 1.8 | 1.97 | 0.59 | | | |
| | 40 mg | | 2.4 | 2.00 | 0.77 | | | |
| 5 | Cpd.(1) | 0 | 1.2 | 1.48 | 0.20 | 12″ | 45″ | 2′03″ |
| | 38 mg | | 1.8 | 1.80 | 0.22 | | | |
| | | | 2.4 | 1.96 | 0.28 | | | |
| 6 | Cpd.(1) | 1/10 | 1.2 | 1.19 | 0.08 | 13″ | 46″ | 2′05″ |
| | 38 mg | | 1.8 | 1.57 | 0.11 | | | |
| | | | 2.4 | 1.83 | 0.18 | | | |
| 7 | Cpd.(2) | 1 | 1.2 | 1.38 | 0.20 | 14″ | 47″ | 2′08″ |
| | 37 mg | | 1.8 | 1.63 | 0.27 | | | |
| | | | 2.4 | 1.77 | 0.37 | | | |
| 8 | Cpd.(3) | 1 | 0.3 | 1.57 | 0.36 | 12″ | 52″ | 2′16″ |
| | 39 mg | | 0.6 | 1.80 | 0.44 | | | |
| | | | 1.2 | 2.05 | 0.65 | | | |

| Processing Composition: | |
|---|---|
| Potassium hydroxide | 67 g |
| Sodium hydroxide | 3.4 g |
| 4-hydroxymethyl-4-methyl-1-p-tolyl-3-pyrazolidone | 13.1 g |
| Sodium Sulfite | 2.0 g |
| 5-methyl benzotriazole | 3.4 g |
| 2-tert-butyl hydroquinone | 0.3 g |
| 2-methyl hydroquinone | 0.1 g |
| Cyclopentanol | 1.0 ml |

In Table 1 figures with respect to the compound use is in terms of the amount/100 cm². Further in Table 1 IP represents time required until a color image begins to appear; $T_{0.5}$ stands for time required until the color image density reaches 50% of that of one hour after the processing; and $T_{0.8}$ stands for time required until the color image density reaches 80% of that of one hour after the processing.

The following are formulas of the brightening agent used in the example and of the DRR compound used in the control samples.

Brightening Agent

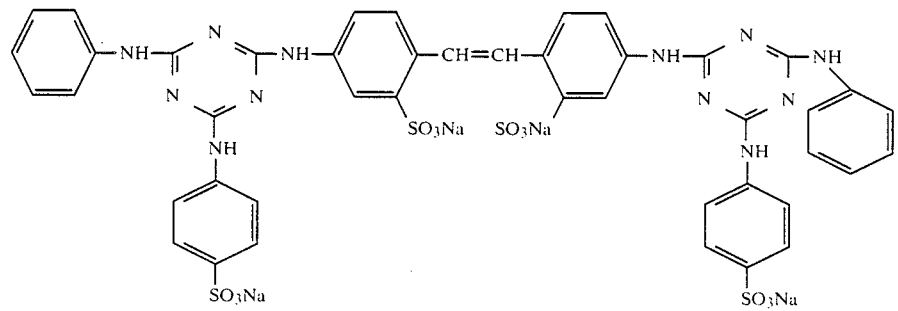

Control Compound (1)

-continued

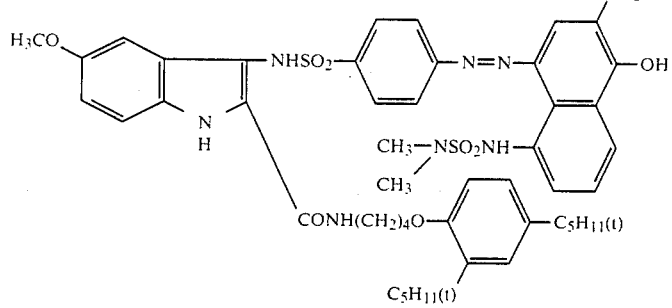

Control Compound (2)

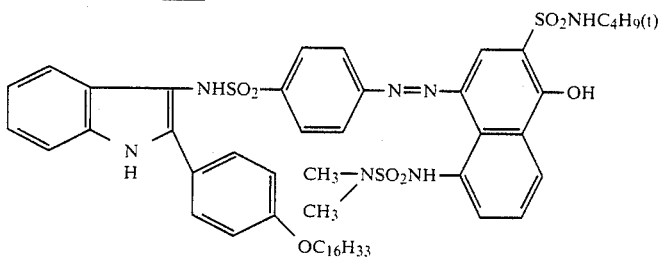

Control Compound (3)

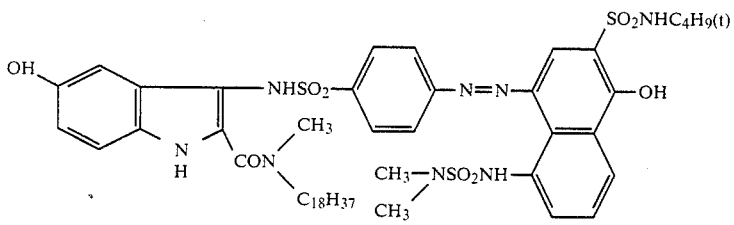

Control Compound (4)

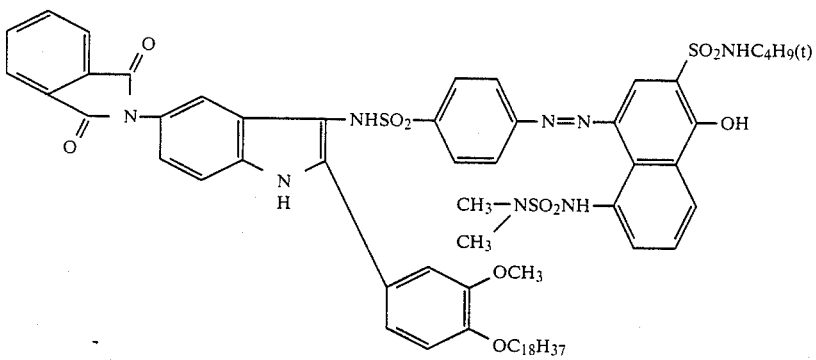

For those samples whose minimum densities were too high to be evaluated, the scavenger, 2,5-dioctyl hydroquinone was added to their compound-containing layers in order to maintain their minimum densities low. To those which have low minimum densities, no scavenger was added. The maximum densities were controlled according to the change in the fogging agent in their emulsion layers.

It is apparent in Table 1 that Sample 1, although it contains no scavenger, does not show any sufficient density in its color image, while Samples 2 and 3, despite of their sufficient densities, tend to produce fog and show that their image forming rate is low.

In contrast thereto, Samples 5,6 and 7, which are according to the present invention, have sufficient densities and little fog, and furthermore, their image forming rate is high. Above all, Samples 5 and 6 which contain Compound(1), despite of the small quantities of the scavenger, give sufficiently white background with large difference between the maximum densities and the minimum densities.

Sample 7 gives sufficient image densities even when the quantity of the fogging agent is small, and shows high image forming rate as compared with Sample 3 which also gives high image densities in the small quantity of the fogging agent, Sample 4, containing a compound having similar structure but different in the direction of Ballast, has low image forming rate. This fact shows that the position of Ballast has a large influence upon the image forming rate.

EXAMPLE 2

A multi-layered light-sensitive element was prepared by coating, in order, the following layers on a 110-micron-thick transparent polyethylene terephthalate film support.

(1) An image receiving layer comprising a poly[styrene-co-N,N,-dimethyl-N-benzyl-N-p-(methacryloylaminophenyl)methyl ammonium chloride-co-divinyl benzene] (molar ratio:48:48:4) (27 mg/100 cm²), brightening agent (0.4 mg/100 cm²) and gelatine (27 mg/100 cm²).

(2) A light reflection layer comprising titanium dioxide (230 mg/100 cm²) and gelatin (22 mg/100 cm²).

(3) An opaque layer comprising carbon black (25 mg/100 cm²) and galatin (17 mg/100 cm²).

(4) A cyan DRR compound-containing layer comprising Exemplified compound (15), which is a cyan DRR compound (4.1 mg/100 cm²), tricresyl phosphate (2.5 mg/100 cm²) and gelatin (11.0 mg/100 cm²).

(5) A red-sensitive light-sensitive layer comprising a red-sensitive internal latent image type direct positive silver bromide emulsion (10 mg/100 cm² in silver), potassium 2-sec-octadecyl hydroquinone-5-sulfonate (1.4 g/mol of silver), 1-[4-(2-formyl hydrazino)phenyl]-3-phenyl-thiourea (1.2 mg/mol of silver) and gelatin (15.5 mg/100 cm²).

(6) An interlayer comprising 2,5-di-sec-dodecyl hydroquinone (4.5 mg/100 cm²), dibutyl phthalate(2.25 mg/100 cm²) and gelatin (10.0 mg/100 cm²).

(7) A magenta DRR compound-containing layer comprising Exemplified compound (!), which is a magenta DRR compound (4.6 mg/100 cm²), tricresyl phosphate (2.5 mg/100 cm²) and gelatin (11.0 mg/100 cm²).

(8) A green-sensitive light-sensitive layer comprising a green- sensitive internal latent image type direct positive silver bromide emulsion (8 mg/100 cm² in silver), potassium 2-sec-octadecyl hydroquinone-5-sulfonate (1.4 g/mol of silver), 1-[4-(2-formyl hydrazino)phenyl]-3-phenyl-thiourea (1.2 mg/mol of silver) and gelatin (13 mg/100 cm²).

(9) An interlayer comprising 2,5-di-sec-dodecyl hydroquinone (4.5 mg/100 cm²), dibutyl phthalate(2.25 mg/100 cm²) and gelatin (10.0 mg/100 cm²).

(10) A yellow DRR compound-containing layer comprising Exemplified compound (17), which is a yellow DRR compound (5.6 mg/100 cm²), tricresyl phosphate (3.0 mg/100 cm²) and gelatin (12 mg/100 cm²).

(11) A blue-sensitive light-sensitive layer comprising a blue-sensitive internal latent image type direct positive silver bromide emulsion (8 mg/100 cm² in silver), potassium 2-sec-octadecyl hydroquinone-5-sulfonate (1.4 g/mol of silver), 1-[4-(2-formyl hydrazino)phenyl]-3-phenyl thiourea (1.2 mg/mol of silver) and gelatin (13 mg/100 cm²).

(12) A protective layer comprising tetrakis(vinyl sulfonylmethyl)methane (2 mg/100 cm²) and gelatin (9mg/100 cm²).

The thus prepared light-sensitive element was subjected, through an optical silver wedge, to exposure to light at a specific amount and the exposed light sensitive element was superposed with the processing sheet prepared in ths same manner as in Example 1, and to the superposed sheets was attached a pod containing the same alkaline processing composition as used in Example 1, to prepare a photographic material unit. This multi-color photographic material unit was put through between forcedly juxtaposed rollers to rupture the pod to spread the contents therein out into between the protective layer (12) and the timing layer (3) of the processing sheet to thereby carry out processing. As a result, a satisfactory color image was obtained after the interval of 3 minutes at the temperature of 23° C.

We claim:

1. A photographic recording material which comprises, on a support, a silver emulsion halide layer and a photographic layer comprising an indole compound represented by the general formula (I):

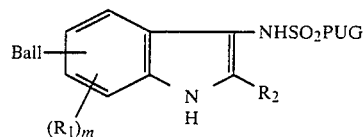

wherein PUG represents a photographically useful group, Ball represents an organic group which has enough molecular weight and/or disposition to render the compound non-diffusible during processing of said photographic recording material with an alkaline medium and wherein said Ball contains a nitrogen atom which is directly attached to the 5th or 6th position an the iodole ring of said indole compound, said Ball being a succinimide group or a phthalimide group, $R_1$ represents a halogen atom or a monovalent organic group, $R_2$ represents a hydrogen atom or a low molecular group attached, through a carbon atom, to the 2nd position of the indole ring and m represents an integer of zero to 3.

2. A photographic recording material according to claim 1, wherein $R_1$ is a halogen atom, an alkyl or an alkoxy group.

3. A photographic recording material according to claim 2, wherein $R_1$ is a halogen atom, an alkyl group having 1 to 3 carbon atoms or an alkoxy group having 1 to 3 carbon atoms.

4. A photographic recording material according to claim 1, wherein $R_2$ is group having from 1 to 9 carbon atoms.

5. A photographic recording material according to claim 4, wherein $R_2$ is an alkyl group having from 1 to 9 carbon atoms, a phenyl group having 1 to 9 carbon atoms or a

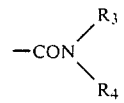

group, wherein $R_3$ and $R_4$ independently represent a hydrogen atom or an alkyl group having from 1 to 4 carbon atoms and provided that said $R_3$ and $R_4$ may form a ring.

6. A photographic recording material according to claim 4, wherein $R_2$ is selected from a phenyl group which is unsubstituted or substituted by a halogen or from the group consisting of an acetylamide group, a methyl sulfonamide group, a nitro group, a carboxy group, a sulfo group, a methane-sulfone group, an alkyl group and an alkoxy group.

7. A photographic recording material according to claim 1, wherein said PUG is a group which is capable of causing a photographic effect.

8. A photographic recording material according to claim 1, wherein said PUG is selected from a group consisting of silver-complex forming agents, silver halide-solving agent, hardeners, fogging agents, anti-foggants, developers, development inhibitors development accelerators, bleach restrainers, bleach accelerators, dyes and dye precursors.

* * * * *